(12) United States Patent
Thompson

(10) Patent No.: US 8,900,289 B2
(45) Date of Patent: *Dec. 2, 2014

(54) STENT WITH DUAL SUPPORT STRUCTURE

(75) Inventor: Paul J. Thompson, New Hope, MN (US)

(73) Assignee: Covidien LP, Mansfield, MA (US)

( * ) Notice: Subject to any disclaimer, the term of this patent is extended or adjusted under 35 U.S.C. 154(b) by 243 days.

This patent is subject to a terminal disclaimer.

(21) Appl. No.: 13/198,770

(22) Filed: Aug. 5, 2011

(65) Prior Publication Data

US 2011/0288633 A1  Nov. 24, 2011

Related U.S. Application Data

(63) Continuation of application No. 12/633,246, filed on Dec. 8, 2009, now Pat. No. 8,007,527, which is a continuation of application No. 11/042,316, filed on Jan. 24, 2005, now Pat. No. 7,632,300, which is a continuation of application No. 10/353,353, filed on (Continued)

(51) Int. Cl.
*A61F 2/06* (2013.01)
*A61F 2/91* (2013.01)
*A61F 2/915* (2013.01)

(52) U.S. Cl.
CPC . *A61F 2/91* (2013.01); *A61F 2/915* (2013.01); *A61F 2002/91508* (2013.01); *A61F 2002/91525* (2013.01); *A61F 2002/91541* (2013.01); *A61F 2002/91558* (2013.01); *A61F 2002/91566* (2013.01)
USPC .......................................... 623/1.15; 623/1.17

(58) Field of Classification Search
CPC ......... A61F 200/852; A61F 2/82; A61F 2/91; A61F 2/915

USPC ...................................... 623/1.15, 1.17, 1.18
See application file for complete search history.

(56) References Cited

U.S. PATENT DOCUMENTS

| | | |
|---|---|---|
| 4,733,665 A | 3/1988 | Palmaz |
| 4,739,762 A | 4/1988 | Palmaz |

(Continued)

FOREIGN PATENT DOCUMENTS

| | | |
|---|---|---|
| DE | 197 22 384 A1 | 12/1998 |
| EP | 0 709 067 A2 | 5/1996 |

(Continued)

OTHER PUBLICATIONS

Antonio L. Bartorelli, et al. "The Sorin Carbostent, Handbook of Coronary Stents, Third Edition,"; pp. 177-179 (2000).

(Continued)

*Primary Examiner* — Bruce E Snow
(74) *Attorney, Agent, or Firm* — Alana T. Bergman, Esq.

(57) ABSTRACT

A intraluminal stent comprises a reticulated tube having an un-deployed diameter and expandable to an enlarged diameter. The tube includes a structural beam extending between first and second ends. The structural beam changes from a first geometry to a second geometry when the tube changes from the un-deployed diameter to the enlarged diameter. The structural beam includes first and second longitudinal elements each extending at least partially between the first and second ends and with a spacing between the first and second elements. Each of said first and second elements changes from the first geometry to the second geometry when the tube changes from the un-deployed diameter to the enlarged diameter for the spacing to remain substantially unchanged as the tube changes from the un-deployed diameter to the enlarged diameter.

16 Claims, 11 Drawing Sheets

Related U.S. Application Data

Jan. 28, 2003, now abandoned, which is a continuation of application No. 09/545,246, filed on Apr. 7, 2000, now Pat. No. 6,533,808, which is a continuation of application No. 09/069,347, filed on Apr. 29, 1998, now Pat. No. 6,132,461, which is a continuation-in-part of application No. 09/049,486, filed on Mar. 27, 1998, now Pat. No. 6,132,460.

(56) References Cited

U.S. PATENT DOCUMENTS

| | | | |
|---|---|---|---|
| 4,760,849 A | 8/1988 | Kropf | |
| 4,768,507 A | 9/1988 | Fischell et al. | |
| 4,776,337 A | 10/1988 | Palmaz | |
| 4,913,141 A | 4/1990 | Hillstead | |
| 5,019,085 A | 5/1991 | Hillstead | |
| 5,026,377 A | 6/1991 | Burton et al. | |
| 5,195,984 A | 3/1993 | Schatz | |
| 5,342,348 A | 8/1994 | Kaplan | |
| 5,419,760 A | 5/1995 | Narciso, Jr. | |
| 5,421,955 A | 6/1995 | Lau et al. | |
| 5,443,500 A | 8/1995 | Sigwart | |
| 5,449,373 A | 9/1995 | Pinchasik et al. | |
| 5,476,508 A * | 12/1995 | Amstrup | 623/1.2 |
| 5,514,154 A | 5/1996 | Lau et al. | |
| 5,540,712 A | 7/1996 | Kleshinski et al. | |
| 5,556,413 A | 9/1996 | Lam | |
| 5,569,295 A | 10/1996 | Lam | |
| 5,591,172 A | 1/1997 | Bachmann et al. | |
| 5,591,197 A | 1/1997 | Orth et al. | |
| 5,649,977 A | 7/1997 | Campbell | |
| 5,695,499 A | 12/1997 | Helgerson et al. | |
| 5,695,516 A | 12/1997 | Fischell et al. | |
| 5,697,971 A | 12/1997 | Fischell et al. | |
| 5,707,386 A | 1/1998 | Schnepp-Pesch et al. | |
| 5,707,387 A | 1/1998 | Wijay | |
| 5,718,713 A | 2/1998 | Frantzen | |
| 5,725,572 A | 3/1998 | Lam et al. | |
| 5,728,131 A | 3/1998 | Frantzen et al. | |
| 5,741,327 A | 4/1998 | Frantzen | |
| 5,759,186 A | 6/1998 | Bachmann et al. | |
| 5,800,526 A | 9/1998 | Anderson et al. | |
| 5,807,404 A | 9/1998 | Richter | |
| 5,810,872 A | 9/1998 | Kanesaka et al. | |
| 5,817,102 A | 10/1998 | Johnson et al. | |
| 5,843,117 A | 12/1998 | Alt et al. | |
| 5,853,419 A | 12/1998 | Imran | |
| 5,855,600 A | 1/1999 | Alt | |
| 5,861,027 A | 1/1999 | Trapp | |
| 5,888,201 A | 3/1999 | Stinson et al. | |
| 5,928,280 A | 7/1999 | Hansen et al. | |
| 5,954,729 A | 9/1999 | Bachmann et al. | |
| 6,001,124 A | 12/1999 | Bachinski | |
| 6,027,527 A | 2/2000 | Asano et al. | |
| 6,042,606 A | 3/2000 | Frantzen | |
| 6,077,295 A | 6/2000 | Limon et al. | |
| 6,083,259 A | 7/2000 | Frantzen | |
| 6,120,522 A | 9/2000 | Vrba et al. | |
| 6,132,460 A | 10/2000 | Thompson | |
| 6,132,461 A | 10/2000 | Thompson | |
| 6,190,406 B1 | 2/2001 | Duerig et al. | |
| 6,203,569 B1 | 3/2001 | Wijay | |
| 6,231,598 B1 | 5/2001 | Berry et al. | |
| 6,273,911 B1 | 8/2001 | Cox et al. | |
| 6,273,913 B1 | 8/2001 | Wright et al. | |
| 6,287,336 B1 | 9/2001 | Globerman et al. | |
| 6,299,635 B1 | 10/2001 | Frantzen | |
| 6,309,414 B1 | 10/2001 | Rolando et al. | |
| 6,312,459 B1 | 11/2001 | Huang et al. | |
| 6,325,825 B1 | 12/2001 | Kula et al. | |
| 6,358,274 B1 | 3/2002 | Thompson | |
| 6,533,808 B1 | 3/2003 | Thompson | |
| 6,558,415 B2 | 5/2003 | Thompson | |
| 6,911,041 B1 * | 6/2005 | Zscheeg | 623/1.15 |
| 7,632,300 B2 | 12/2009 | Thompson | |
| 2001/0016770 A1 | 8/2001 | Allen et al. | |

FOREIGN PATENT DOCUMENTS

| | | |
|---|---|---|
| EP | 0 732 088 A2 | 9/1996 |
| EP | 0 800 800 A1 | 10/1997 |
| EP | 0 830 853 A1 | 3/1998 |
| EP | 0 997 115 A2 | 5/2000 |
| FR | 2 764 794 A1 | 12/1998 |
| WO | WO 99/21509 A1 | 5/1999 |
| WO | WO 99/39660 A1 | 8/1999 |
| WO | WO 99/49810 A1 | 10/1999 |

OTHER PUBLICATIONS

Dunitz, M., Excerpts from "Handbook of Coronary Stents," Rotterdam Thoraxcentre Group, University Hospital Dijkzigt, Rotterdam, The Netherlands, 23 pages (1997).

An Extended European Search Report corresponding to European Application No. EP 10 18 6231.6, completed Aug. 22, 2011 and mailed Sep. 1, 2011; 9 pages.

An Extended European Search Report corresponding to European Application No. EP 10 18 6236.5, completed Aug. 22, 2011 and mailed Sep. 6, 2011; 9 pages.

* cited by examiner

FIG. 10 —PRIOR ART—

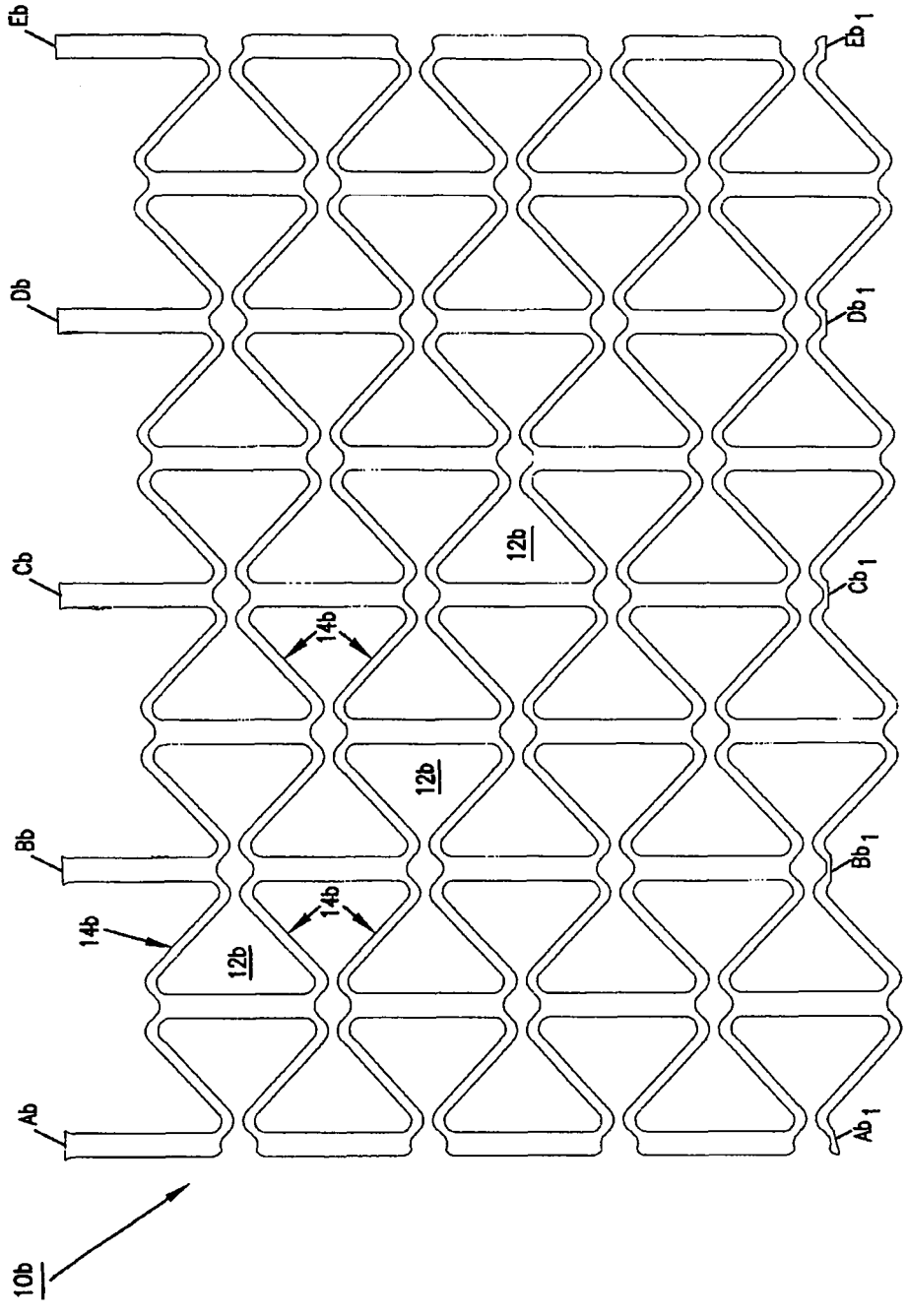
FIG. 12 --PRIOR ART--

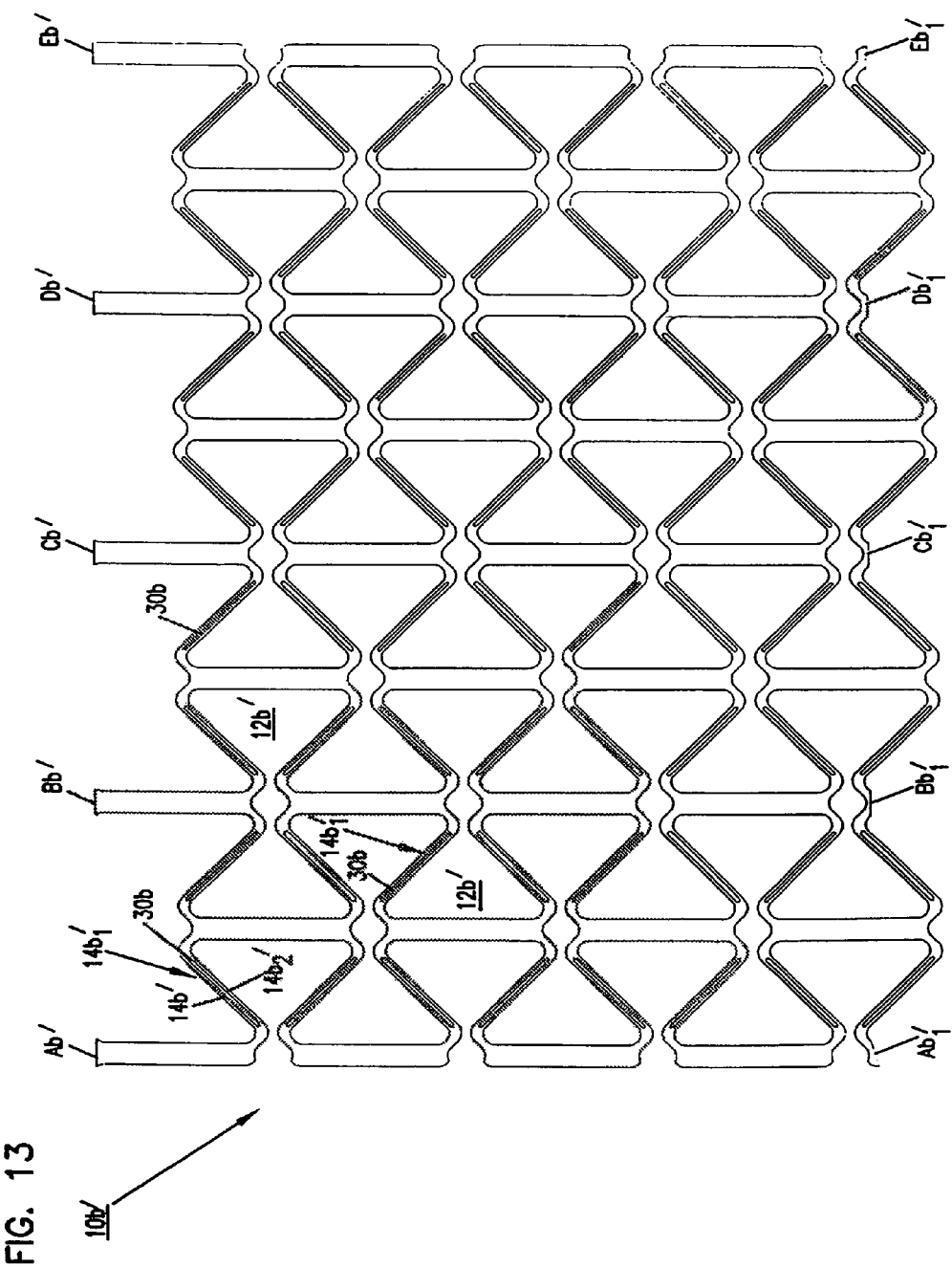

STENT WITH DUAL SUPPORT STRUCTURE

I. CROSS REFERENCE TO RELATED APPLICATIONS

This application is a continuation application of U.S. patent application Ser. No. 12/633,246, filed Dec. 8, 2009, now U.S. Pat. No. 8,007,527 which is a continuation application of U.S. patent application Ser. No. 11/042,316, filed Jan. 24, 2005, which issued as U.S. Pat. No. 7,632,300 on Dec. 15, 2009, which is a continuation of U.S. patent application Ser. No. 10/353,353, filed Jan. 28, 2003, now abandoned, which is a continuation of U.S. patent application Ser. No. 09/545,246, filed Apr. 7, 2000, which issued as U.S. Pat. No. 6,533,808 on Mar. 18, 2003, which is a continuation of application Ser. No. 09/069,347, filed Apr. 29, 1998, which issued as U.S. Pat. No. 6,132,461 on Oct. 17, 2000, which is a continuation-in-part of application Ser. No. 09/049,486, filed Mar. 27, 1998, which issued as U.S. Pat. No. 6,132,460 on Oct. 17, 2000, the entire contents of which are incorporated herein by this reference.

II. BACKGROUND OF THE INVENTION

1. Field of the Invention

This invention pertains to stents for use in intraluminal applications. More particularly, this invention pertains to a novel structure for such stents.

2. Description of the Prior Art

Stents are widely used for numerous applications where the stent is placed in the lumen of a patient and expanded. Such stents may be used in coronary or other vasculature, as well as other body lumens.

Commonly, stents are cylindrical members. The stents expand from reduced diameters to enlarged diameters. Frequently, such stents are placed on a balloon catheter with the stent in the reduced-diameter state. So placed, the stent is advanced on the catheter to a placement site. At the site, the balloon is inflated to expand the stent to the enlarged diameter. The balloon is deflated and removed, leaving the enlarged diameter stent in place. So used, such stents are used to expand occluded sites within a patient's vasculature or other lumen.

Examples of prior art stents are numerous. For example, U.S. Pat. No. 5,449,373 to Pinchasik et al. teaches a stent with at least two rigid segments joined by a flexible connector. U.S. Pat. No. 5,695,516 to Fischell teaches a stent with a cell having a butterfly shape when the stent is in a reduced-diameter state. Upon expansion of the stent, the cell assumes a hexagonal shape.

In stent design, it is desirable for the stent to be flexible along its longitudinal axis to permit passage of the stent through arcuate segments of a patient's vasculature or other body lumen. Preferably, the stent will have at most minimal longitudinal shrinkage when expanded and will resist compressive forces once expanded.

III. SUMMARY OF THE INVENTION

According to a preferred embodiment of the present invention, an intraluminal stent is disclosed. The stent comprises a reticulated tube having an un-deployed diameter and expandable to an enlarged diameter. The tube includes a structural beam extending between first and second ends. The structural beam changes from a first geometry to a second geometry when the tube changes from the un-deployed diameter to the enlarged diameter. The structural beam includes first and second longitudinal elements each extending at least partially between the first and second ends and with a spacing between the first and second elements. Each of said first and second elements changes from the first geometry to the second geometry when the tube changes from the un-deployed diameter to the enlarged diameter for the spacing to remain substantially unchanged as the tube changes from the un-deployed diameter to the enlarged diameter.

IV. BRIEF DESCRIPTION OF THE DRAWINGS

FIG. 12 is a plan view of a second prior art stent as it would appear if it were longitudinally split and laid out flat; and FIG. 13 is the view of FIG. 12 with the stent modified for support beams to include parallel, spaced elements in accordance with the present invention.

V. DESCRIPTION OF THE PREFERRED EMBODIMENT

Referring now to the several drawing figures in which identical elements are numbered identically, a description of the preferred embodiment of the present invention will now be provided. Where several embodiments are shown, common elements are similarly numbered and not separately described with the addition of apostrophes to distinguish the embodiments.

As will be more fully described, the present invention is directed to a novel support beam for an expandable stent. The support beam is applicable to a wide variety of stent designs. In a preferred embodiment, the support beam will be used as a longitudinal segment in a stent as described in the aforementioned U.S. patent application Ser. No. 09/049,486 filed Mar. 27, 1998, entitled "STENT" and naming Paul J. Thompson as sole inventor. Therefore, such a stent will now be described with reference to FIGS. 1 to 9. Subsequently, the use of the novel beam will be described in use with other stent designs (i.e., those shown in U.S. Pat. No. 5,449,373 to Pinchasik et al. and U.S. Pat. No. 5,695,516 to Fischell) to illustrate the broad range of applicability of the novel support beam to a wide range of other stent designs.

Figure 1:
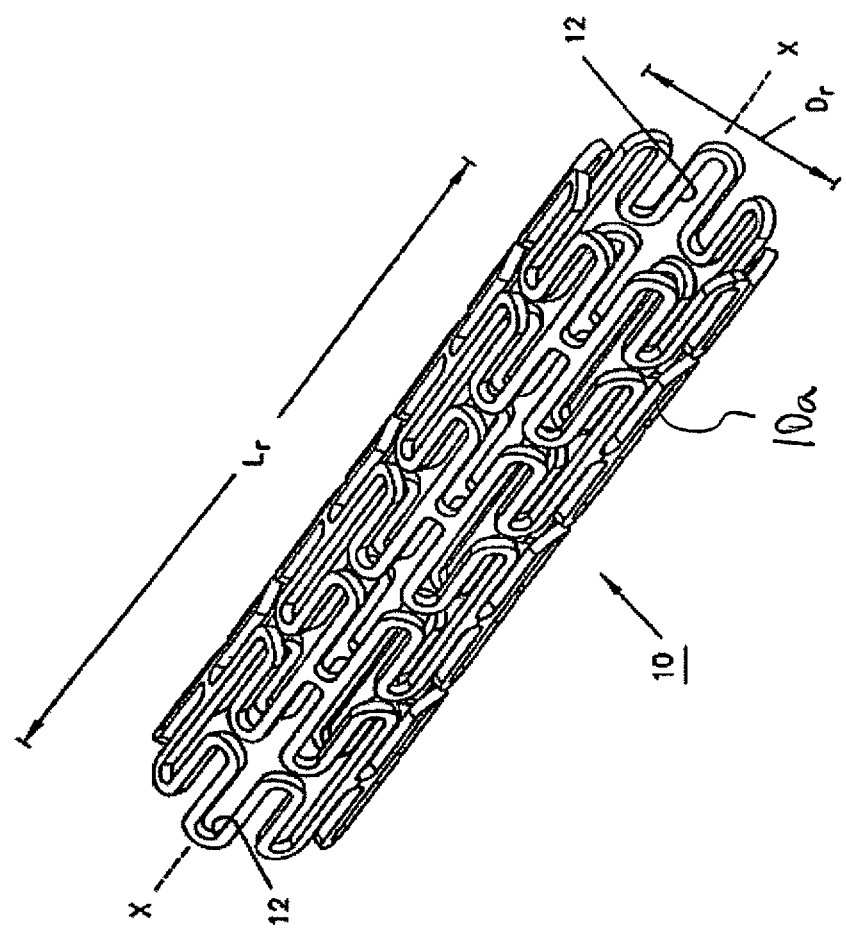
FIG. 1 is a perspective view of a first embodiment of a stent according to the present invention shown in a rest diameter state and showing a plurality of stent cells each having a major axis perpendicular to an axis of the stent.

FIG. 1 illustrates a stent 10 including a stent body 10a having a rest length L, and an un-deployed or reduced diameter $D_r$. The stent 10 is of the design shown in the aforementioned U.S. patent application. The slot of the novel beam construction, as will be described, is not shown in FIG. 1.

Figure 2:
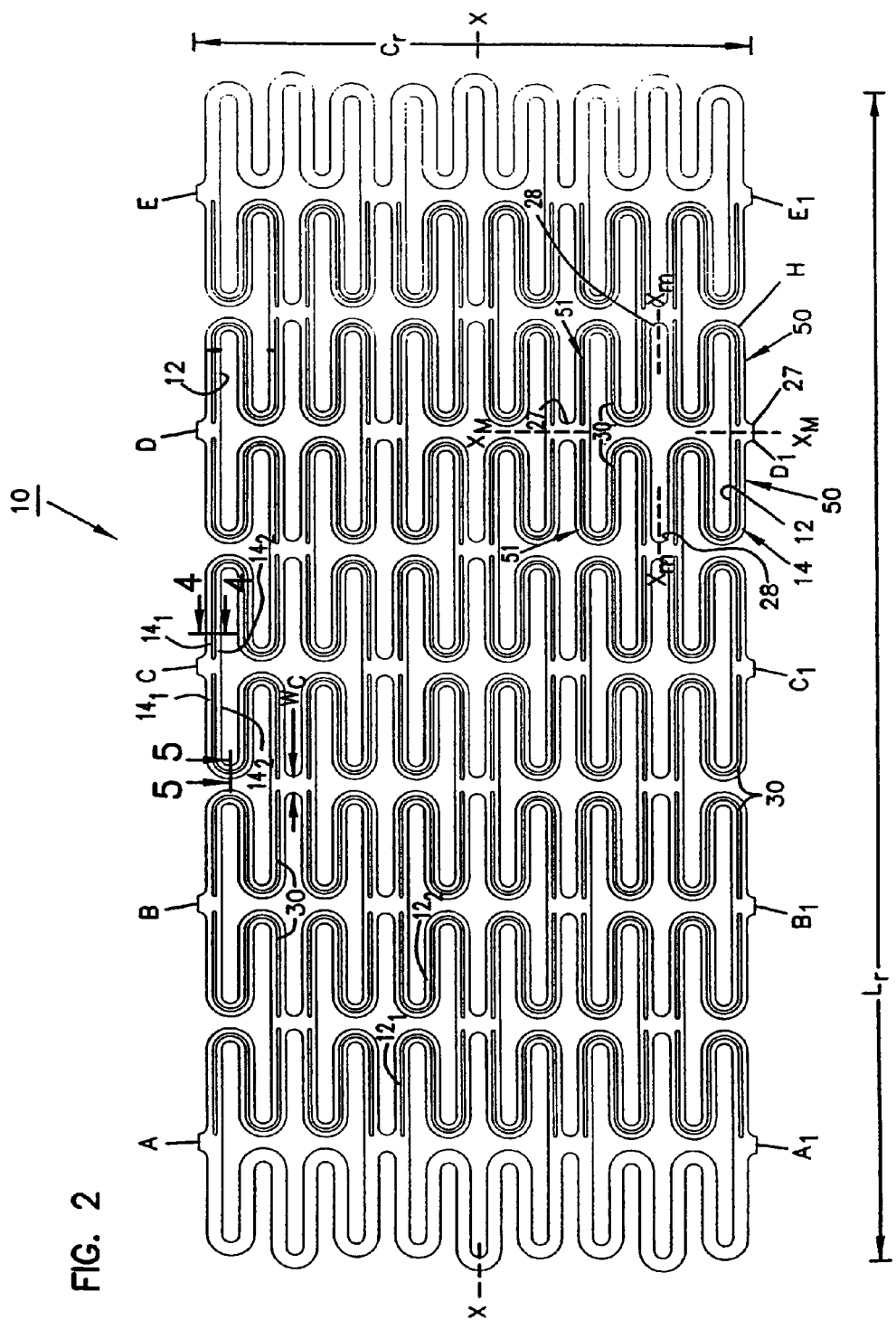
FIG. 2 is a plan view of the stent of FIG. 1 as it would appear if it were longitudinally split and laid out flat.
Figure 6:
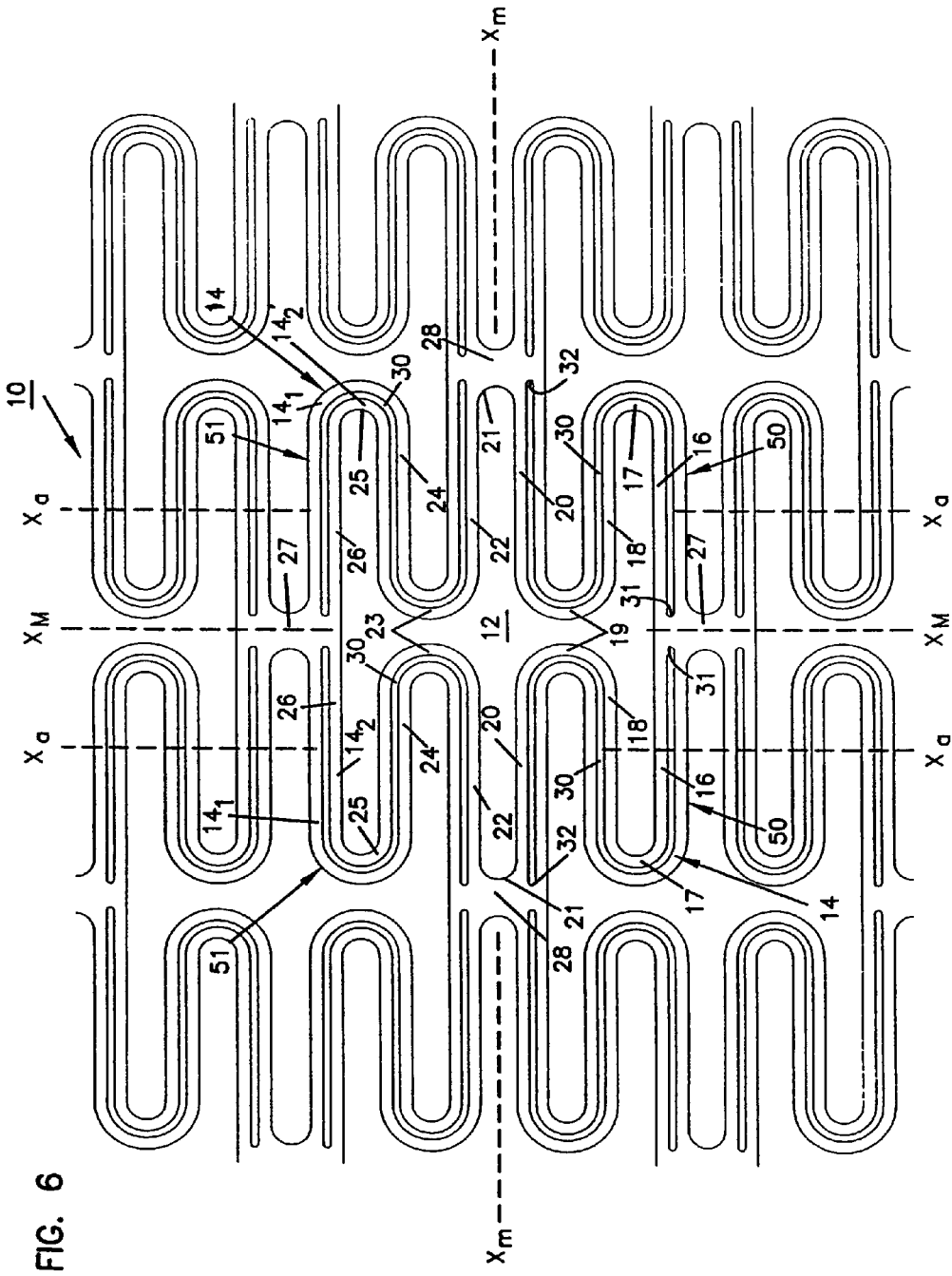
FIG. 6 is an enlarged view of a portion of FIG. 2 illustrating a cell structure with material of the stent surrounding adjacent cells shown in phantom lines.

For ease of illustration, the stent 10 is shown flat in FIG. 2 which illustrates a rest circumference $C_r$ ($C_r=nD_r$). In FIG. 2, locations A, B, C, D and E are shown severed from their normally integrally formed locations $A_1$, $B_1$, $C_1$, $D_1$ and $E_1$. This permits the stent 10 to be shown as if it were severed at normally integrally formed locations $A-A_1$, $B-B_1$, $C-C_1$, $D-D_1$ and $E-E_1$ and laid flat. FIG. 6 is an enlarged portion of the view of FIG. 2 to better illustrate a cell structure as will be described.

Figure 3:
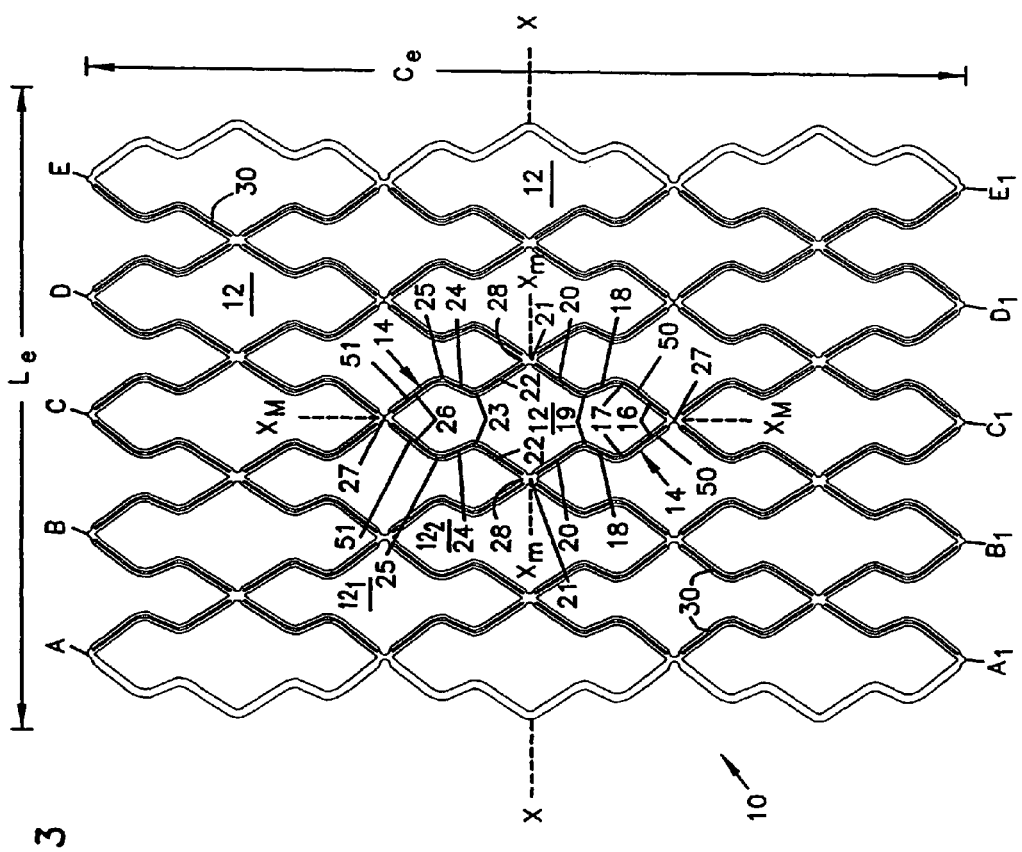
FIG. 3 is the view of FIG. 2 following expansion of the stent to an enlarged diameter.

The stent 10 is a reticulated, hollow tube. The stent 10 may be expanded from the rest diameter D, (and corresponding rest circumference $C_r$) to an expanded or enlarged diameter. FIG. 3 is a view similar to FIG. 2 (i.e., illustrating the expanded stent 10 as it would appear if longitudinally split and laid flat). Since FIG. 3 is a two-dimensional representation, the enlarged diameter is not shown. However, the enlarged circumference $C_e$ is shown as well as a length $L_e$ following expansion. The expanded diameter is equal to $C_e/\pi$.

As will be discussed length $L_e$ is preferably not more than minimally smaller (e.g., less than 10% smaller) than length $L_r$. Ideally, $L_e$ equals $L_r$.

The material of the stent 10 defines a plurality of cell defining portions or cells 12. The cells 12 are bounded areas which are open (i.e., extend through the wall thickness of the stent 10). The stent 10 may be formed through any suitable means including laser or chemical milling. In such processes, a hollow cylindrical tube is milled to remove material and form the open cells 12.

Figure 8:
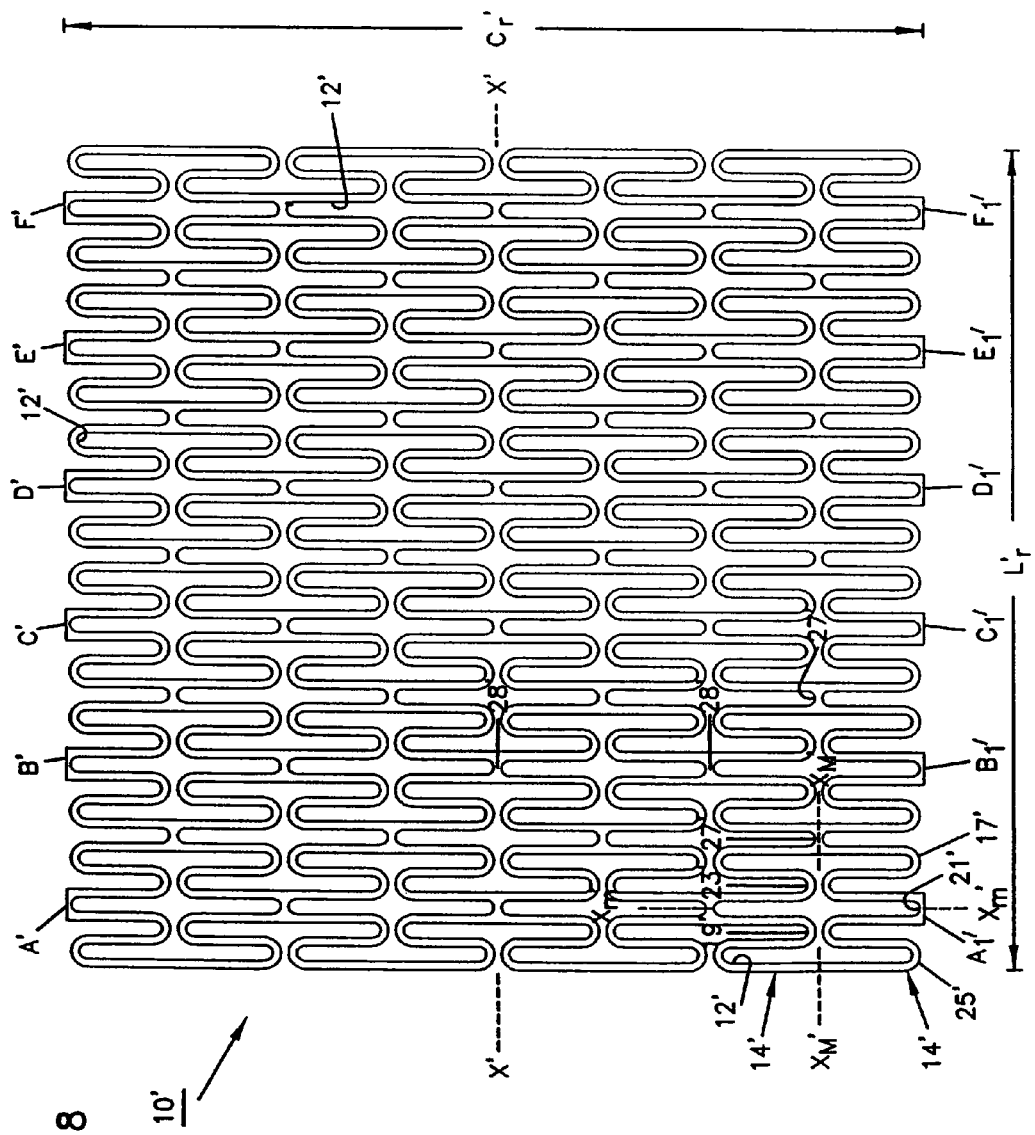
FIG. 8 is the view of FIG. 2 showing an alternative embodiment of the present invention with a major axis of the cell being parallel to an axis of the stent.
Figure 9:
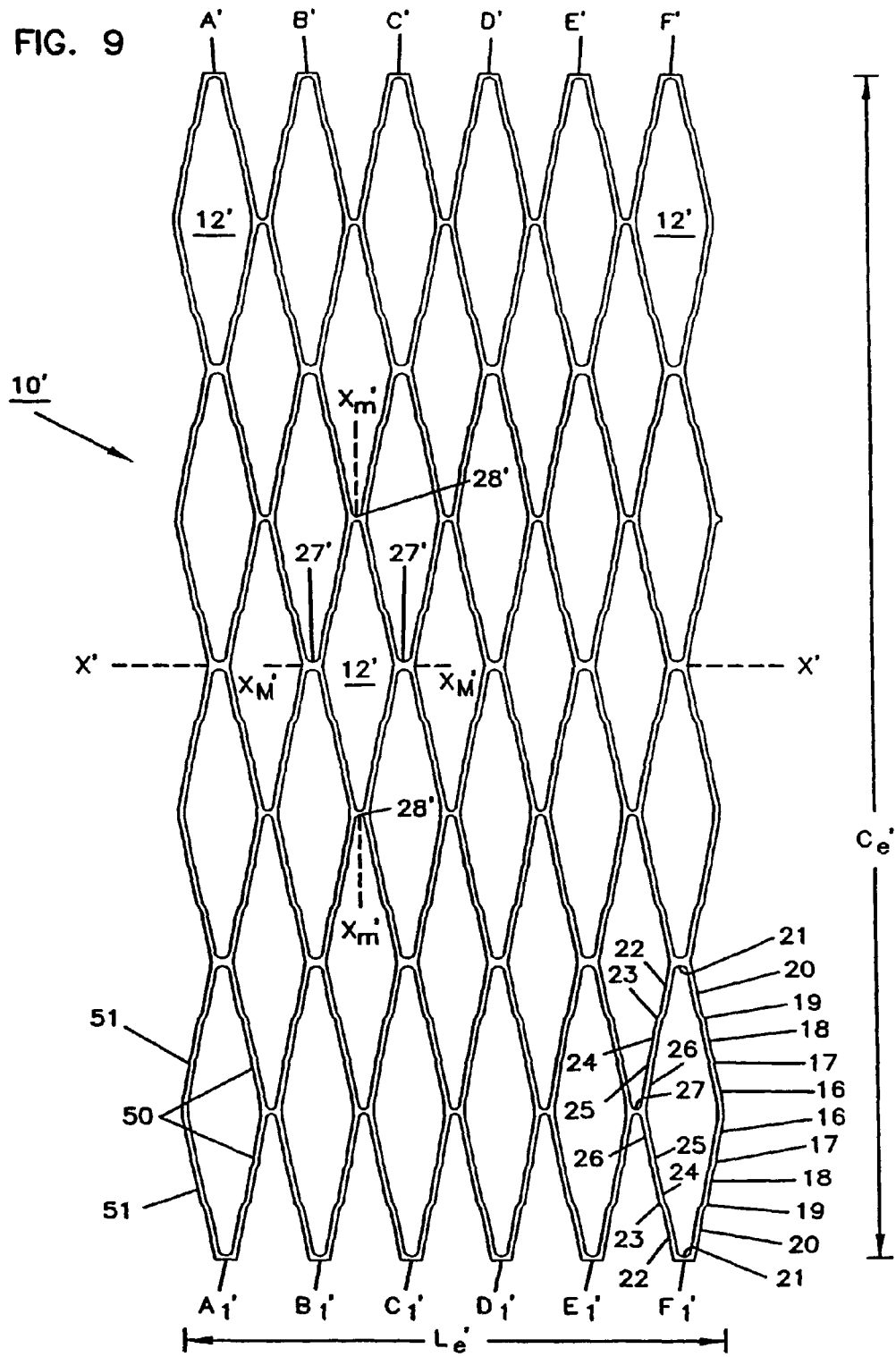
FIG. 9 is the view of FIG. 5 following expansion of the stent to an enlarged diameter.

The cells 12 have a longitudinal or major axis $X_M$-$X_M$ and a transverse or minor axis $X_m$-$X_m$. In the embodiments of FIGS. 1-3, the major axis $X_M$-$X_M$ is perpendicular to the longitudinal cylindrical axis X-X of the stent 10. In the embodiments of FIGS. 8 and 9, the major axis $X_M'$-$X_M'$ is parallel to the longitudinal cylindrical axis X'-X' of the stent 10'. The cell 12 is symmetrical about axes $X_M$-$X_M$ and $X_m$-$X_m$.

The cell 12 is defined by portion of the tube material including first and second segments or first and second longitudinal segments or support beams 14. The beams 14 each have a longitudinal axis $X_a$-$X_a$ (shown in FIG. 6). The beams' longitudinal axes Xa-Xa are parallel to and positioned on opposite sides of the cell major axis $X_M$-$X_M$.

Referring to FIG. 6, each of longitudinal beams 14 has an undulating pattern to define a plurality of peaks 17, 21, 25 and valleys 19, 23. The peaks 17, 21, 25 are spaced outwardly from the longitudinal axes $X_a$-$X_a$ and the valleys 19, 23 are spaced inwardly from the longitudinal axes $X_a$-$X_a$. As used in this context, "inward" and "outward" mean toward and away from, respectively, the cell's major axis $X_M$-$X_M$.

Each of the peaks 17, 21, 25 and valleys 19, 23 is a generally semi-circular arcuate segment. The peaks 17, 21, 25 and valleys 19, 23 are joined by parallel and spaced-apart straight segments 16, 18, 20, 22, 24 and 26 which extend perpendicular to the major axis $X_M$-$X_M$. Linearly aligned straight end portions 16, 26 of opposing segments 14 are joined at first and second longitudinal connection locations 27 spaced apart on the major axis $X_M$-$X_M$. First and second transverse connection locations 28 are spaced apart on the minor axis $X_m$-$X_m$. The first and second transverse connection locations 28 are positioned at the apices of the center peaks 21 of the longitudinal beams 14.

Slots 30 are formed through the complete thickness of each of the beams 14. The slots 30 extend between first and second ends 31, 32. The first ends 31 are adjacent the longitudinal connection locations 27. The second ends 32 are adjacent the transverse connection locations 28. The slots 30 divide the beams 14 into first and second parallel elements $14_1$, $14_2$.

Figure 4:
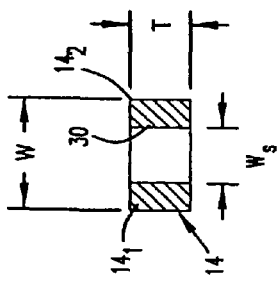
FIG. 4 is a view taken along line 4-4 in FIG. 2.
Figure 5:
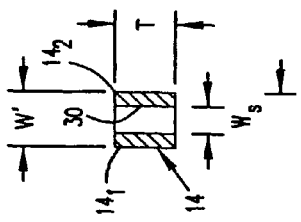
FIG. 5 is a view taken along line 5-5 in FIG. 2.

Except as will be described, the beams 14 have uniform cross-sectional dimensions throughout their length as illustrated in FIG. 4. By way of non-limiting example, the width W and thickness T of the straight line segments 16, 18, 20, 22, 24 and 26 are about 0.0065 inch (about 0.16 mm) and about 0.0057 inch (about 0.14 mm), respectively. The width W includes the widths (each of equal width) of the two elements $14_1$, $14_2$ plus the width $W_s$ of the slot 30. By way of a non-limiting example, the width $W_s$ is in the range of 0.001 to 0.0025 inch. By way of another non-limiting example, the width $W_s$ is less than 0.005 inch.

For reasons that will be described, the width W' (FIG. 5) at the apices of the peaks 17, 21, 25 and valleys 19, 23 is narrower than width W (in the example given, narrow width W' is about 0.0055 inch or about 0.13 mm). The width of the peaks 17, 21, 25 and valleys 19, 23 gradually increases from width W' at the apices to width W at the straight segments 16, 18, 20, 22, 24 and 26. At the longitudinal and transverse connection locations 27, 28, the width $W_c$ (shown in FIG. 2) is preferably equal to or less than the common width W. Preferably, the width $W_s$ of slot 30 remains constant throughout its length.

The combined lengths of segments 16-20 to the apex of peak 21 represent a path length 50 from longitudinal connection location 27 to transverse connection location 28. Similarly the combined lengths of the other arcuate and straight segments 22-26 to the apex of peak 21 represent identical length path lengths 51 of identical geometry from longitudinal connection locations 27 to transverse connection locations 28. Each of the path lengths 50, 51 is longer than a straight-line distance between the transverse and longitudinal connection locations 27, 28. As will be described, the straight-line distance between the transverse and longitudinal connection locations 27, 28 increases as the diameter of the stent 10 is expanded. The path lengths 50, 51 are sized to be not less than the expanded straight-line distance.

The stent 10 includes a plurality of identical cells 12. Opposite edges of the segments 14 define obliquely adjacent cells (such as cells $12_1$, $12_2$ in FIG. 2). Cells 12 having major axes $X_M$-$X_M$ collinear with the major axis $X_M$-$X_M$ of cell 12 are interconnected at the longitudinal connection locations 27. Cells having minor axes collinear with the minor axis $X_m$-$X_m$ of cell 12 are interconnected at the transverse connection locations 28.

As mentioned, the stent 10 in the reduced diameter of FIG. 1 is advanced to a site in a lumen. The stent 10 is then expanded at the site. The stent 10 may be expanded through any conventional means. For example, the stent 10 in the reduced diameter may be placed on the balloon tip of a catheter. At the site, the balloon is expanded to generate radial forces on the interior of the stent 10. The radial forces urge the stent 10 to radially expand without appreciable longitudinal expansion or contraction. Plastic deformation of the material of the stent 10 (e.g., stainless steel) results in the stent 10 retaining the expanded shape following subsequent deflation of the balloon. Alternatively, the stent 10 may be formed of super-elastic or shape memory material (such as nitinol—a well-known stent material which is an alloy of nickel and titanium).

As the stent 10 expands, the path lengths 50, 51 straighten to accommodate the expansion. During such change in geometry of the path lengths 50, 51, each of the elements $14_1$, $14_2$ similarly changes in geometry so that. At all times, the elements $14_1$, $14_2$ are mutually parallel and separated by spacing 30.

FIG. 3 illustrates the straightening of the path lengths 50, 51. In FIG. 3, the stent 10 has been only partially expanded to an expanded diameter less than a maximum expanded diameter. At a maximum expanded size, the path lengths 50, 51 are fully straight. Further expansion of the stent 10 beyond the maximum expanded size would result in narrowing of the minor axis $X_m$-$X_m$ (i.e., a narrowing of a separation between the transverse connection locations and a resulting narrowing of the length $L_r$, of the stent) or would require stretching and thinning of the stent material.

As shown in FIG. 3, during expansion of the stent 10, the straight segments 16, 18, 20, 22, 24 and 26 are substantially unchanged. The straightening of the path lengths 50, 51 results in bending of the arcuate peaks 17, 21, 25 and valleys 19, 23. Since the width W' of the peaks 17, 21, 25 and valleys 19, 23 is less than the width W of the straight segments 16, 18, 20, 22, 24 and 26, the arcuate peaks 17, 21, 25 and valleys 19, 23 are less stiff than the straight segments 16, 18, 20, 22, 24 and 26 and, therefore, more likely to deform during expansion.

As the geometry of the beams 14 changes during expansion, the geometry of the first and second elements $14_1$, $14_2$ similarly changes so that the elements $14_1$, $14_2$ remain in mutually parallel relation both before and after expansion. As used in this application, the term "mutually parallel" means the spacing 30 between the elements $14_1$, $14_2$ is substantially constant throughout the length of the elements $14_1$, $14_2$. The elements $14_1$, $14_2$ and beam 14 may be curved or straight throughout their lengths.

As the stent 10 expands, the cells 12 assume a diamond shape shown in FIG. 3. Since the expansion forces are radial, the length of the major axis $X_M$-$X_M$ (i.e., the distance between the longitudinal connection locations 27) increases. The length of the minor axis $X_m$-$X_m$, (and hence the length of the stent 10) remains unchanged.

The stent 10 is highly flexible. To advance to a site, the axis X-X of the stent 10 must bend to navigate through a curved lumen. Further, for placement at a curved site in a lumen, the stent 10 must be sufficiently flexible to retain a curved shape following expansion and to bend as the lumen bends over time. The stent 10, as described above, achieves these objections.

When bending on its axis X-X, the stent 10 tends to axially compress on the inside of the bend and axially expand on the outside of the bend. The present design permits such axial expansion and contraction. The novel cell geometry 12 results in an accordion-like structure which is highly flexible before and after radial expansion. Further, the diamond shape of the cells 12 after radial expansion resists constricting forces otherwise tending to collapse the stent 10.

The dual support structure of the elements separated by the slots increases flexibility without reducing resistance to compression forces. Further, during expansion and during flexing of the stent on its axis, the use of parallel, spaced elements $14_1$, $14_2$ results in lower stress levels than would be experienced by a solid beam.

Numerous modifications are possible. For example the stent 10 may be lined with either an inner or outer sleeve (such as polyester fabric or ePTFE) for tissue growth. Also, the stent may be coated with radiopaque coatings such as platinum, gold, tungsten or tantalum. In addition to materials previously discussed, the stent may be formed of any one of a wide variety of previous known materials including, without limitation, MP35N, tantalum, platinum, gold, Elgiloy and Phynox.

Figure 7:
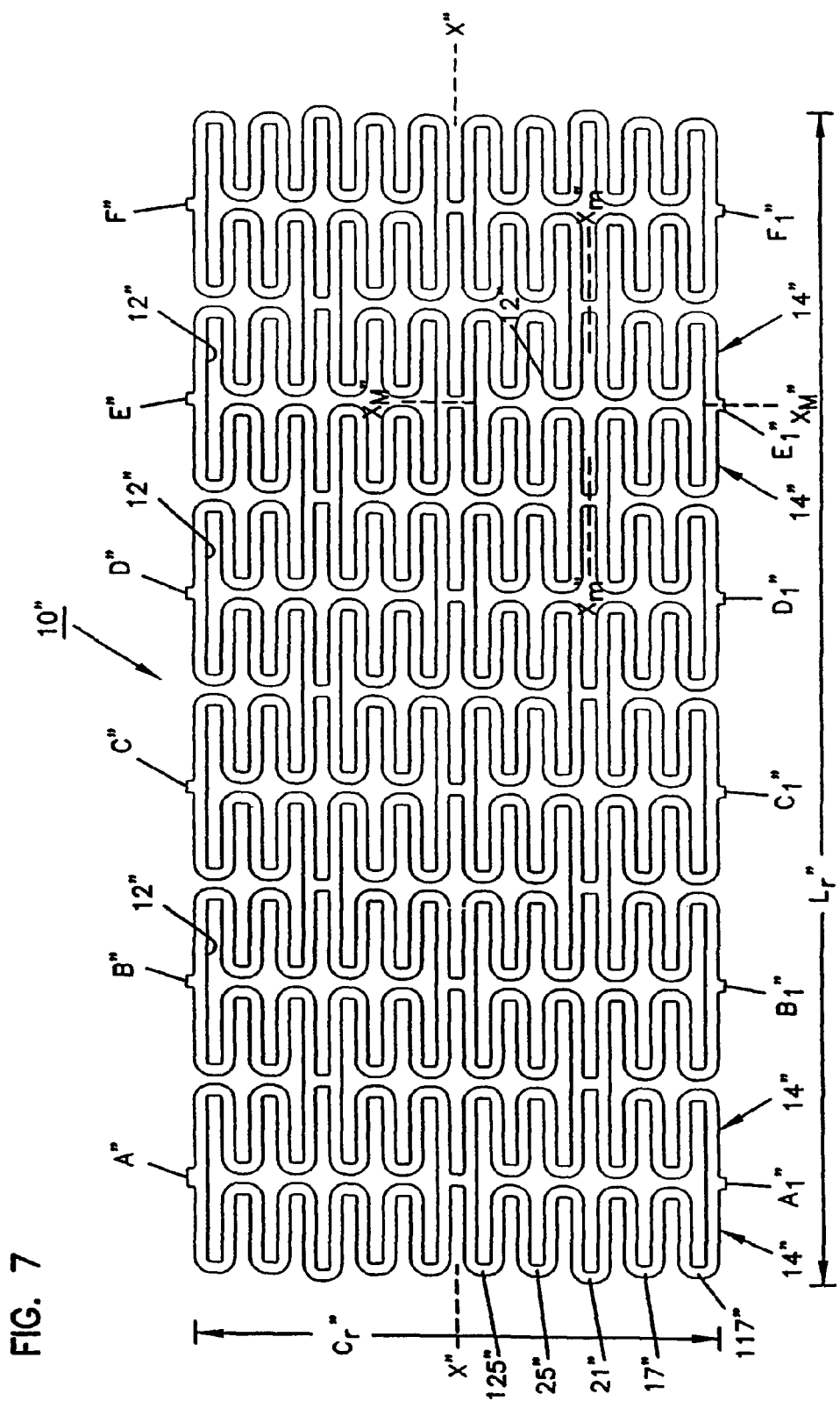
FIG. 7 is the view of FIG. 2 showing an alternative embodiment of the present invention with a cell having five peaks per longitudinal segment.

While three cells 12 are shown in FIG. 2 longitudinally connected surrounding the circumference $C_r$ of the stent, a different number could be so connected to vary the properties of the stent 10 as a designer may elect. Likewise, while each column of cells 12 in FIG. 2 is shown as having three longitudinally connected cells 12, the number of longitudinally connected cells 12 could vary to adjust the properties of the stent. Also, while each longitudinal segment 14 is shown as having three peaks 17, 21, 25 per longitudinal segment 14, the number of peaks could vary. FIG. 7 illustrates a stent 10" with a cell 12" having five peaks 117", 17", 21", 25" and 125" per longitudinal segment 14". Preferably, the longitudinal segment will have an odd number of peaks so that the transverse connection points are at an apex of a center peak. In FIG. 7, no slot is shown in the beams 14" for ease of illustration.

FIGS. 8 and 9 illustrate an alternative embodiment where the major axis $X_M'$-$X_M'$ of the cells 12' are parallel with the cylindrical axis X'-X' of the stent 10'. In FIG. 9, the expanded stent 10' is shown at a near fully expanded state where the path lengths 50', 51' are substantially linear. In FIGS. 8 and 9, no slots are shown in the beams 14' for ease of illustration.

Figure 10:
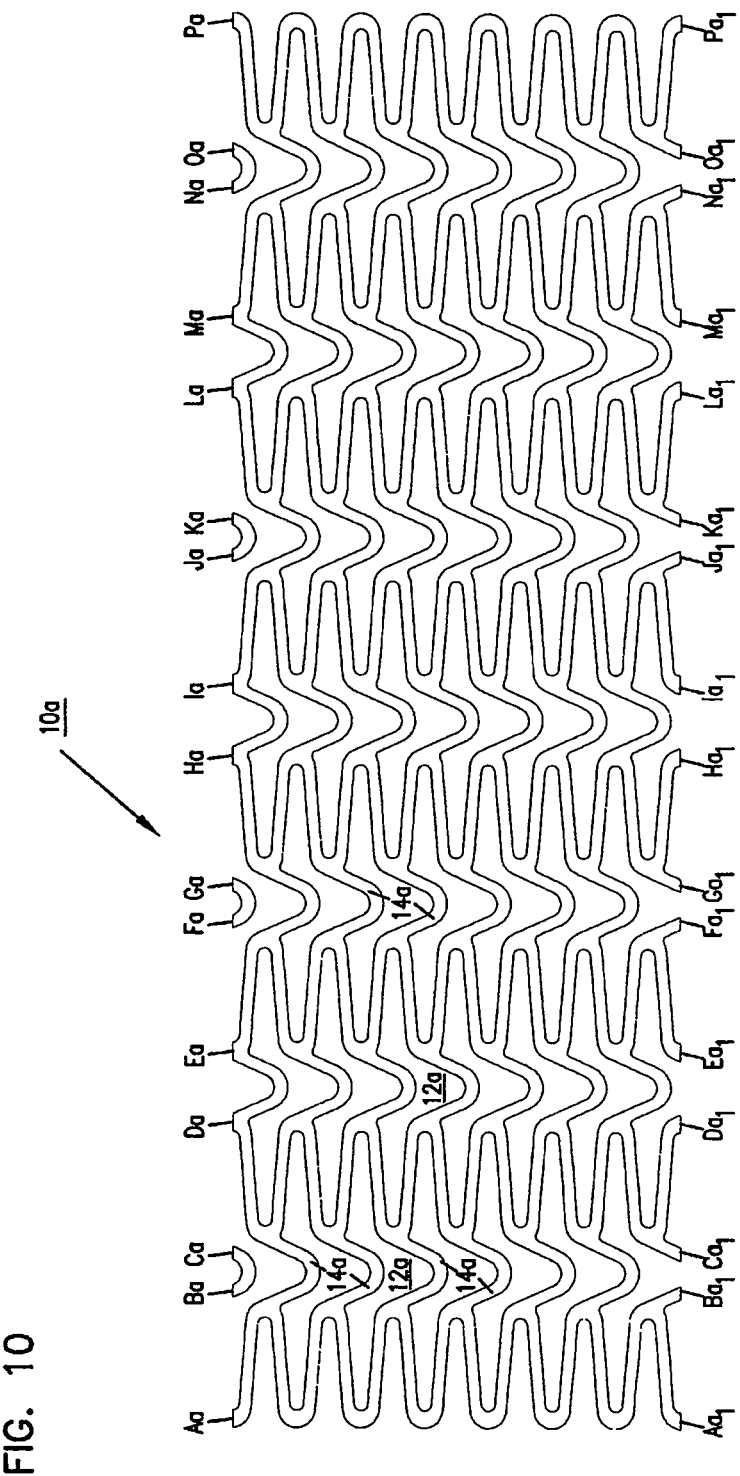
FIG. 10 is a plan view of a first prior art stent as it would appear if it were longitudinally split and laid out flat.

FIGS. 10 and 12 illustrate prior art stent designs. FIG. 10 is a stem 10a as shown in U.S. Pat. No. 5,449,373 to Pinchasik et al. and FIG. 12 is a stent 10b as shown in U.S. Pat. No. 5,695,516 to Fischell. Stent 10a is shown flat as if longitudinally split at locations Aa-$Aa_1$ through Pa-$Pa_1$. Similarly, Stent 10b is shown flat as if longitudinally split at locations Ab-$Ab_1$ through Eb-$Eb_1$.

Both of the designs of FIGS. 10 and 12 include solid structural beams 14a, 14b. Beams 14a are curved when the stent 10a is in a reduced diameter state. The beams 14a cooperate to define cells 12a. The curved beams 14a straighten when the stent 10a expands. The beams 14b are straight and cooperate to define a butterfly-shaped cell 12b. Upon expansion, the beams 14b remain straight but pivot for the cell 12b to assume a hexagon shape upon expansion.

Figure 11:
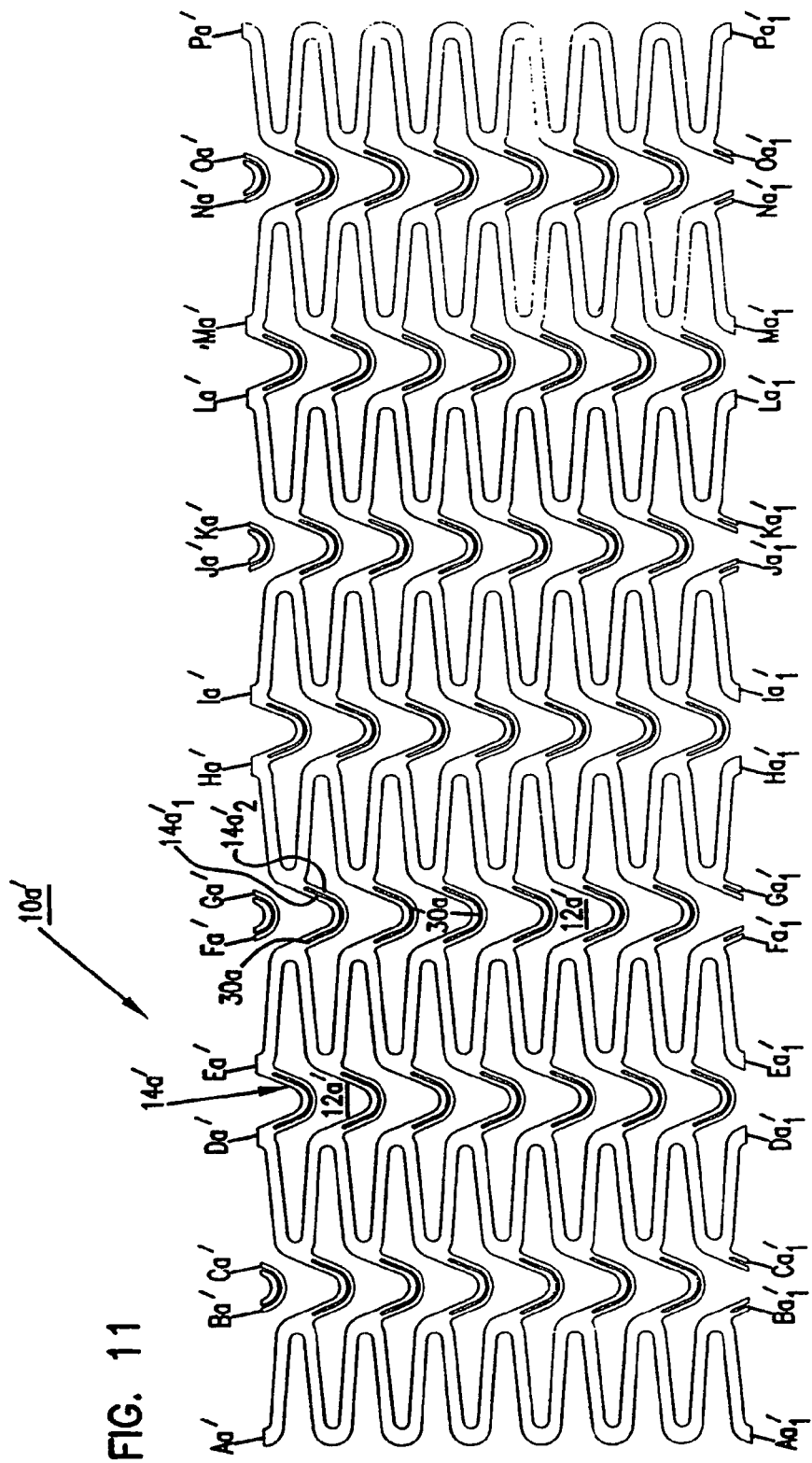
FIG. 11 is the view of FIG. 10 with the stent modified for support beams to include parallel, spaced elements in accordance with the present invention.

The dual support structure aspect of the present invention is applicable to prior art stents such as those shown in FIGS. 10 and 12. FIGS. 11 and 13 show the prior art stents of FIGS. 10 and 11, respectively, modified according to the dual support structure aspect of the present invention. Specifically, beams 14a', 14b' are provided with slots 30a, 30b to divide the beams into parallel, spaced first and second elements $14a_1'$, $14a_2'$ and $14b_1'$, $14b_2'$ having the benefits previously described.

From the foregoing, the present invention has been shown in a preferred embodiment. Modifications and equivalents are intended to be included within the scope of the appended claims.

What is claimed is:

1. A stent comprising:
a stent body defining a longitudinal axis, the stent body being expandable from a first, unexpanded orientation to a second, expanded orientation, the stent body including:
a plurality of cell defining portions, each of the cell defining portions defining a length and a major axis that extends along the length, each of the cell defining portions including first and second segments, the first and second segments each extending about the stent body in an undulating pattern, wherein in the first, unexpanded orientation of the stent body, the undulating pattern includes a plurality of peaks and valleys joined by spaced-apart straight segments that are parallel to each other, the spaced-apart straight segments defining a length that extends perpendicular to the major axis of a respective one of the cell defining portions;

a pair of first connection locations positioned on circumferentially opposite sides of at least one of the cell defining portions of the plurality of cell defining portions for connecting the at least one cell defining portion to a circumferentially adjacent one of the cell defining portions; and a pair of second connection locations positioned on axially opposite sides of the at least one cell defining portion for connecting the at least one cell defining portion to an axially adjacent cell defining portion, wherein each of the first and second segments includes first and second spaced-apart elements extending from one of the first connection locations to one of the second connection locations and defining the undulating pattern.

2. The stent of claim 1, wherein the first and second segments are configured such that spacing between the first and second spaced-apart elements remains substantially unchanged as the stent body is expanded from the first, unexpanded orientation to the second, expanded orientation.

3. The stent of claim 2, wherein each of the plurality of cell defining portions is substantially identical.

4. The stent of claim 2, wherein each of the plurality of cell defining portions assumes a diamond shape as the stent body expands from the first, unexpanded orientation to the second, expanded orientation.

5. The stent of claim 2, wherein the first and second spaced-apart elements are substantially parallel to one another in the first, unexpanded orientation and remain substantially parallel to one another as the stent body expands from the first, unexpanded orientation to the second, expanded orientation.

6. The stent of claim 1, wherein the stent body is made of a material that is balloon expandable.

7. The stent of claim 1, wherein the stent body is made of a shape memory material.

8. The stent of claim 7, wherein the shape memory material is nitinol.

9. A stent comprising:

a stent body defining a longitudinal axis and having cell defining portions, each of the cell defining portions defining a length and a major axis that extends along the length, each of the cell defining portions including first and second segments, the first and second segments being interconnected at opposite ends thereof, the first and second segments each defining an axis and an undulating pattern that includes a plurality of peaks and valleys spaced outwardly and inwardly, respectively, from the axes of the respective first and second segments, the plurality of peaks and valleys joined by spaced-apart straight segments that are parallel to each other, the spaced-apart straight segments defining a length that extends perpendicular to the major axis of a respective one of the cell defining portions when the stent body is disposed in an unexpanded orientation;

the stent body including first and second connection locations at interconnection points of the first and second segments and third and fourth connection locations on the first and second segments, the third and fourth connection locations being transverse to the first and second connection locations; and each of the first and second segments including first and second spaced-apart elements extending from one of the connection locations to one of the other connection locations and defining the undulating pattern.

10. The stent of claim 9, wherein the first and second segments are configured such that spacing between the first and second spaced-apart elements remains substantially unchanged as the stent body is expanded from the unexpanded orientation to an expanded orientation.

11. The stent of claim 10, wherein the cell defining portions are substantially identical.

12. The stent of claim 10, wherein the cell defining portions assume a diamond shape as the stent body expands from the unexpanded orientation to the expanded orientation.

13. The stent of claim 10, wherein the first and second spaced-apart segments are substantially parallel segments and remain substantially parallel as the stent body expands from the unexpanded orientation to the expanded orientation.

14. The stent of claim 9, wherein the stent body is made of a material that is balloon expandable.

15. The stent of claim 9, wherein the stent body is made of a shape memory material.

16. The stent of claim 15, wherein the shape memory material is nitinol.

* * * * *